United States Patent
Stickler et al.

(10) Patent No.: US 8,062,234 B2
(45) Date of Patent: Nov. 22, 2011

(54) PH SENSOR

(75) Inventors: David James Stickler, Whitechurch Cardiff (GB); Mark Geoffrey John Waters, Bridgend (GB)

(73) Assignee: University College Cardiff Consultants Limited, South Glamorgan (GB)

( * ) Notice: Subject to any disclaimer, the term of this patent is extended or adjusted under 35 U.S.C. 154(b) by 1086 days.

(21) Appl. No.: 11/630,650

(22) PCT Filed: Jun. 23, 2005

(86) PCT No.: PCT/GB2005/002456
§ 371 (c)(1),
(2), (4) Date: Aug. 6, 2007

(87) PCT Pub. No.: WO2006/000764
PCT Pub. Date: Jan. 5, 2006

(65) Prior Publication Data
US 2008/0294069 A1  Nov. 27, 2008

(30) Foreign Application Priority Data
Jun. 24, 2004 (GB) .................................. 0414222.0

(51) Int. Cl.
*A61B 5/00* (2006.01)
*B65D 81/00* (2006.01)
*A61M 1/00* (2006.01)
*A61F 5/44* (2006.01)
*H01H 29/02* (2006.01)
*H01H 29/20* (2006.01)

(52) U.S. Cl. ........ 600/584; 600/573; 600/574; 604/318; 604/327; 604/330; 200/206

(58) Field of Classification Search .................. 600/573, 600/574, 584; 604/318, 327, 330; 200/206
See application file for complete search history.

(56) References Cited

U.S. PATENT DOCUMENTS

| | | | |
|---|---|---|---|
| 3,351,050 A * | 11/1967 | Naftolin ........................ | 600/574 |
| 3,373,735 A | 3/1968 | Gallagher | |
| 4,212,153 A * | 7/1980 | Kydonieus et al. ............ | 368/62 |
| 4,248,597 A * | 2/1981 | McNeely ....................... | 116/206 |
| 4,631,061 A * | 12/1986 | Martin .......................... | 604/318 |
| 4,728,607 A * | 3/1988 | Dorn et al. ..................... | 435/34 |
| 4,846,005 A * | 7/1989 | Bacehowski et al. ....... | 73/864.81 |
| 4,847,128 A * | 7/1989 | Dorn et al. ..................... | 435/34 |
| 5,053,339 A * | 10/1991 | Patel ................................ | 436/2 |
| 5,063,930 A * | 11/1991 | Nucci ............................ | 600/366 |
| 5,094,955 A * | 3/1992 | Calandra et al. ............ | 435/288.7 |
| 5,096,813 A * | 3/1992 | Krumhar et al. ................ | 435/28 |
| 5,166,990 A | 11/1992 | Riccitelli et al. | |
| 5,254,473 A * | 10/1993 | Patel ............................... | 436/1 |
| 5,300,049 A * | 4/1994 | Hogan .......................... | 604/317 |
| 5,465,713 A * | 11/1995 | Schoendorfer ............... | 600/346 |

(Continued)

FOREIGN PATENT DOCUMENTS
DE  3504527 A1  2/1986
(Continued)

*Primary Examiner* — Max Hindenburg
*Assistant Examiner* — Sean Dougherty
(74) *Attorney, Agent, or Firm* — Banner & Witcoff, Ltd.

(57) ABSTRACT

The invention relates to a pH sensor for use in a catheter drainage system. The invention also relates to a catheter, drainage bag or connection unit comprising the pH sensor of the present invention, methods of using the pH sensor and methods of making the pH sensor.

30 Claims, 5 Drawing Sheets

U.S. PATENT DOCUMENTS

| | | | |
|---|---|---|---|
| 5,498,528 A * | 3/1996 | King | 435/34 |
| 5,554,147 A | 9/1996 | Batich et al. | |
| 5,897,834 A * | 4/1999 | Lawrence et al. | 422/424 |
| 5,945,830 A * | 8/1999 | Magowan et al. | 324/438 |
| 6,113,856 A * | 9/2000 | Lawrence et al. | 436/166 |
| 6,287,518 B1 * | 9/2001 | Ignacio et al. | 422/86 |
| 6,299,583 B1 | 10/2001 | Eggers et al. | |
| 6,428,748 B1 * | 8/2002 | Wallach | 422/56 |
| 6,576,474 B2 * | 6/2003 | Wallach | 436/169 |
| 6,623,418 B2 * | 9/2003 | Smith | 600/3 |
| 6,772,708 B2 * | 8/2004 | Klofta et al. | 116/206 |
| 6,860,984 B2 * | 3/2005 | Bannigan et al. | 205/787.5 |
| 6,921,647 B2 * | 7/2005 | Kritzman et al. | 435/12 |
| 2002/0034475 A1 * | 3/2002 | Ribi | 424/9.6 |
| 2002/0125133 A1 * | 9/2002 | Bannigan et al. | 204/433 |
| 2002/0128542 A1 | 9/2002 | Van Over | |
| 2003/0068824 A1 * | 4/2003 | Frankel et al. | 436/60 |
| 2003/0164136 A1 * | 9/2003 | Klofta et al. | 116/206 |
| 2003/0166293 A1 | 9/2003 | Kritzman et al. | |
| 2004/0115319 A1 * | 6/2004 | Morris et al. | 426/231 |
| 2004/0265440 A1 * | 12/2004 | Morris et al. | 426/231 |
| 2005/0090014 A1 * | 4/2005 | Rao et al. | 436/166 |
| 2005/0199177 A1 * | 9/2005 | Klofta et al. | 116/206 |
| 2006/0030771 A1 * | 2/2006 | Levine et al. | 600/424 |
| 2006/0079740 A1 * | 4/2006 | Silver et al. | 600/309 |
| 2006/0084848 A1 * | 4/2006 | Mitchnick | 600/301 |
| 2006/0127561 A1 * | 6/2006 | Griffin et al. | 427/2.1 |
| 2007/0003993 A1 * | 1/2007 | Kritzman et al. | 435/12 |
| 2007/0287989 A1 * | 12/2007 | Crawford et al. | 604/507 |
| 2008/0041394 A1 * | 2/2008 | Swann et al. | 128/831 |
| 2008/0091153 A1 * | 4/2008 | Harvie | 604/318 |
| 2009/0069671 A1 * | 3/2009 | Anderson | 600/424 |

FOREIGN PATENT DOCUMENTS

| | | |
|---|---|---|
| EP | 0 577 038 A | 1/1994 |
| GB | 2 395 128 A | 5/2004 |
| WO | WO 94/10553 A1 | 5/1994 |
| WO | WO 03/105942 A | 12/2003 |

\* cited by examiner

PH SENSOR

The present invention relates to a pH sensor for use in a catheter drainage system. The present invention also relates to a catheter, drainage bag or connection unit comprising the pH sensor of the present invention, methods of using the pH sensor and methods of making the pH sensor.

The care of many of the elderly and disabled patients undergoing long-term bladder catheterisation is complicated by the encrustation and blockage of their catheters. The problem is unpredictable and community nurses are called out at any time of the night or day to patients in discomfort with urinary retention or incontinent of urine owing to sudden blockage of the catheter. Current methods of controlling the encrustation are ineffective, and generally the replacement catheters block recurrently and the patient gains a reputation as a "blocker"[1].

Encrustation results from infection of the catheterised urinary tract by urease producing organisms, particularly *Proteus mirabilis*. The bacterial urease generates ammonia from urea and the urine becomes alkaline (pH 8-9). *P. mirabilis* also colonizes the catheter surfaces and forms a biofilm. In the alkaline conditions calcium and magnesium phosphates crystallise from the urine and crystalline biofilms develop on the catheters [2]. It should be noted that commonly the urine of these patients is infected with organisms such as *Escherichia coli* which are not urease producers and their metabolism generates slightly acid urine (pH 5-6).

After 2-3 weeks of catheterisation, infection is generally always present within a patient in a benign state. Antibiotics are not used as the infection will reappear when use is stopped. In long-term catheterisation patients, and as indicated above, biofilms of bacteria grow on the catheters and in some cases crystalline biofilms form, which block the catheter, this results in bladder expansion, kidney reflux, septic shock and in some cases death. Crystals can break off the biofilms and can cause side effect such as bladder stones. Additionally, in patients with spinal injuries or neurological disorders, stroke can occur. 50% of long-term patients suffer from encrustation. A UK study [3] of 467 catheterised patients being cared for in the community, recorded 507 emergency referrals related to catheter blockage over a 6 month period. Therefore there are huge costs both financially and in terms of morbidity associated with this problem and there is no current way of avoiding this problem.

There is a need for a simple sensor that could be incorporated into a catheter drainage system to signal that urease producing bacteria have infected the urine, thus giving an early warning signal of impending catheter encrustation and blockage.

It has been know that the detection of changes in pH of various body fluids may be desirable and a number of pH sensors have been devised. In International Patent Application WO 02/096286, a device for insertion into the urethra and that measures pH, $pO_2$ or $pCO_2$ is disclosed. This device is complicated and requires the pH sensor to be inserted into the urethra. Complicated electronic sensor equipment is also required in order to determine if there is a pH change.

US Patent Application US 2002/0128542 discloses a pH indicator comprising a photodetector set in a glass matrix with a processing device. The device is positioned internally within an animal to determine rumen pH.

U.S. Pat. No. 5,596,988 discloses an indicator set into a biphasic material for measurement of blood parameters. The device is positioned within the body.

U.S. Pat. No. 5,704,353 discloses an internally positioned sensor for measuring various parameters. The sensor is connected to optical cables so that changes in the various parameters can be monitored.

U.S. Pat. No. 5,607,417 discloses a pH sensitive matrix which releases an agent when a certain pH is reached.

International Patent Application WO 94/10553 discloses a fibre-optic probe for measuring pH and carbon dioxide levels. The device has a complicated construction and is for insertion into a body cavity.

German Patent Application DE-A-3504527 discloses a urine collection bag with an indicator unit which can be used to quickly determine a pH value.

There are a number of problems with the prior art devices. Firstly, a number of the devices require the use of complicated cables or signalling systems to enable any change in the parameter being measured to be detected. This is particularly a problem when the device is located internally within the human or animal body. A further problem is that the prior art devices do not distinguish between a sustained change in the level of the parameter being measured and a transitory change. Transitory changes in the pH of urine can occur due to a number of factors such as diet; however, a sustained increase in pH is indicative of impending catheter encrustation and blockage. A further problem with the prior art devices is that the pH indicator can leach out of the device due to the flow of urine. Such leaching will reduce the effectiveness of the pH indicator and also contaminate the urine.

The present inventors have endeavoured to solve one or more of the problems associated with the prior art devices. In particular, the inventors have endeavoured to produce sensors from polymeric materials that have been impregnated with pH indicators. The sensors are preferably designed so that they are located in the drainage system of a catheter so that they are clearly visible to the patient/carer enabling the sensor to be continuously monitored. A change from the acid to alkaline reaction will signal infection by *P. mirabilis* or related urease producing organisms and indicate that action should be taken to avoid an acute clinical episode.

The present invention provides a pH sensor for incorporation into a catheter drainage system wherein the pH sensor comprises a polymer matrix comprising a chemically bound pH indicator, wherein in use the pH indicator only responds to a sustained increase in pH.

The pH sensor can be used to detect a sustained increase in pH in its immediate vicinity. In particular, the pH sensor can be used to detect a change in the pH of a fluid (i.e. urine) coming into contact with the sensor or within a bacterial biofilm formed on the sensor, and thereby provide an indication of impending catheter encrustation and blockage. Any transitory increases in pH will not be detected and false positives will be avoided. Furthermore, by having the pH indicator chemically bound, preferably covalently bound, to the polymer matrix, it has been found that no leaching of the pH indicator from the matrix occurs. The pH sensor therefore remains functional during use.

It has been found that the pH sensor of the present invention can be used to detect a change in pH of urine in a catheter system indicating that the urine is infected with urease producing bacteria (e.g., *P. mirabilis*), which is an indicator of impending catheter encrustation and blockage. It has also been found that urease producing bacteria (e.g. *P. mirabilis*) present in urine form a biofilm on the pH sensor. The formation of the biofilm on the pH sensor leads to a sustained increase in pH within the biofilm which is detected by the pH sensor. Due to the fact that the urease producing bacteria form a biofilm on the sensor, the presence of such bacteria can be detected before the overall pH of the urine is increased. In particular, it has been found that the pH sensor responds to a sustained increase in pH (about pH 9) within the biofilm formed on the sensor, while the pH of the urine is at a non-indicative pH of about 6 to 7. Accordingly, it is a particular advantage of the pH sensor of the present invention that a biofilm of urease producing bacteria can form on the pH sensor and that the pH sensor can detect a substantial change in pH within the biofilm, which is an early indicator of impending catheter encrustation and blockage.

The term "chemically bound" means that the pH indicator is bound within the polymer matrix by some form of chemical interaction, such as ionic interaction, hydrogen bonds, etc. Preferably the term means covalently bound.

The term "catheter drainage system" refers to a catheter and the drainage unit. The drainage unit is defined as the drainage bag and drainage bag tubing for connection to the catheter.

The pH sensor of the present invention can be incorporated into the catheter drainage system at any position provided that it is visible to the patient or carer. By being visible any change in the pH indicator can be readily observed. The pH sensor may be positioned close to the inserted end of the catheter while still being visible to the patient or carer. Preferably the pH sensor is positioned in the urine drainage bag. (See FIG. 4, right column.) Such positioning gives the strongest and most rapid signal that encrustation is taking place on the catheter. In an alternative preferred embodiment, the pH sensor is positioned at the junction between the catheter and the drainage bag tubing. (See FIG. 4, left column.) The pH sensor may be positioned at the end of the catheter that is connected to the drainage bag tubing or may be positioned in the end of the drainage bag tubing that connects to the catheter. The pH sensor may be positioned within a connection unit that connects the catheter and the tubing of the drainage bag together.

The pH sensor can be any shape provided it can be positioned into a catheter drainage system and comes into contact with urine. Preferably the pH sensor is a flat disc that can be positioned within the drainage bag. (See FIG. 4, right column.) Preferably the pH sensor can be inserted into a drainage bag. Alternatively, the pH sensor is an annular ring that is sized to be held within the lumen of a tube of the catheter drainage system and has a bore allowing fluid to pass through the sensor. (See FIG. 4, left column.) In a further alternative embodiment, the pH sensor can be in the form of a strip which is printed onto the inner surface of the catheter drainage system. The pH sensor may be printed onto the catheter drainage system using any technique, such as jet printing.

The polymer matrix can be any suitable matrix provided the pH indicator can be chemically bound and provided a biofilm of urease producing bacteria can form on its surface. The polymer matrix ensures that only a sustained change in pH is measured. The rate of diffusion of ions through the polymer matrix enabling it to come into contact with the bound pH indicator is tailored so that only a sustained change in pH will trigger a change in the pH indicator. The amount of polyethylene glycol plasticiser within the polymer matrix used in the examples described herein has a direct influence on the rate of movement of ions through the matrix and controls the response rate of the sensor and thus is set at a level to ensure the desirable response. One skilled in the art can determine the required rate of ion diffusing of the matrix in order to ensure that only a sustained change in pH is measured. Preferably, the type of polymer used must have suitable reactive groups to enable chemical binding of a sulphuric acid treated pH indicator. Preferred polymer matrixes include silicone rubber, polyurethane and cellulose acetate. Most preferably, the polymer matrix is cellulose acetate.

The matrix may be prepared in such a way that it allows or encourages the formation of the biofilm. For example, the matrix may be rough in texture so it is conducive to biofilm binding. The material chosen to make the matrix may have a naturally rough texture, or it may be roughened.

The pH indicator can be any agent that produces a visible signal (e.g. a colour change) in response to an increase in pH that is indicative of impending catheter encrustation and blockage. Urine is normally about pH 6, but when this is raised above pH 7.6, there is a danger of catheter encrustation and blockage. Suitable pH indicators include neutral red, bromothymol blue, cresol red, phenol red, 3-(m-)nitrophenol, fluorescein and rosolic acid. When a biofilm of *Proteus mirabilis* or similar urease producing organisms are formed on the pH sensor, a local pH of 8 to 10 is produced indicating there is a danger of catheter encrustation. Details of the range at which colour transition occurs for these preferred indictors as well as other indicators with lower and higher pH ranges that may be used are described in Table 1 below.

TABLE 1

| pH indicator | pH range | colour transition |
| --- | --- | --- |
| bromocresol purple | 5.2-6.8 | yellow-purple |
| chlorophenol red | 5.4-6.8 | yellow-red |
| neutral red | 6.8-8.0 | red-yellow |
| bromothymol blue | 6.2-7.6 | yellow-blue |
| cresol red | 7.2-8.8 | yellow-red |
| m-cresol purple | 7.4-9.0 | yellow-purple |
| phenol red | 6.4-8.0 | yellow-red |
| 3-(m-)nitrophenol | 6.6-8.6 | colourless-yellow/orange |
| thymol blue | 8.0-9.6 | yellow-blue |
| cresolphthalein | 7.8-9.0 | colourless-pink |
| fluorescein | 7.0-9.0 | yellow-orange |
| Rosolic acid | 6.8-8.0 | yellow-red |
| α-naphtholbenzene | 9.0-11 | yellow-blue |

Preferably the pH indicator is bromothymol blue.

The pH indicator may change colour in response to an increase in pH of urine or of the bacterial biofilm that may develop on the pH sensor. Preferably the pH indicator changes colour in response to an increase in pH of the bacterial biofilm. This indicates infection by the urease producing bacterium *Proteus mirabilis* and impending catheter blockage by encrustation.

The pH indicator can be chemically bound to the matrix using a technique that retains the functionality of the pH indicator. A preferred way of chemically bonding the pH indicator to the matrix is to first react to sulphuric acid ultimately leading to reactive vinylsulfonyl groups which can bind to hydrolysed cellulose acetate. Such coupling is a standard technique well known to those skilled in the art.

The pH sensor preferably comprises between 1 and 5% w/v pH indicator.

The term "sustained increase in pH" as used herein means that an increased pH level is maintained for more than 6 hours, preferably for more than 9 hours and most preferably for more that 12 hours. If an increased pH level is maintained for more than 6, 9 or 12 hours, it is more likely that the change in pH is due to urease-producing bacteria causing encrustation of the catheter rather than any other factor (e.g. diet).

The pH sensor of the present invention may, depending on the matrix used, comprise a matrix stabiliser to improve the retention of the pH indicator. It is advantageous to retain the pH indicator so that the effectiveness of the pH indicator is maintained during use. Furthermore, leaching of the pH indicator from the pH sensor will contaminate the fluid passing over the sensor. Various matrix stabilisers can be used, such as Scotchlite and quaternary ammonium compounds such as hexadecyltributyl ammonium bromide. Quaternary ammonium compounds can be used as surface-active agents and are strongly adsorbed by many substances. They produce positively charged ions in solution and help retention of pH indicators when deprotonation has occurred.

In a particularly preferred embodiment, the pH sensor of the present invention comprises cellulose acetate as the matrix and bromothymol blue as the pH indicator. In addition polyethylene glycol may be incorporated as a plasticizer which adds flexibility to the matrix and also influences the rate of response of the sensor to an increase in pH. It has been found that this combination is particularly good at detecting a sustained increase in pH that is indicative of impending catheter encrustation and blockage.

The pH sensor of the present invention may be provided in combination with a reference material to assist one with determining whether the visual signal (e.g. colour change) indicating that there is a sustained increase in pH has been obtained. The reference material is preferably fused to the pH sensor. For example, when the visual signal is a colour change, the reference material may be the colour of the pH sensor before and/or after a sustained increase in pH. Preferably, the reference material is the colour of the pH sensor after a sustained increase in pH. If the colour of the pH sensor and the reference material are identical, then there has been a sustained increase in pH. When the pH sensor is applied as a printed strip, it may be bordered by reference strips. The reference strips may be printed on the inner surface or outer surface of the catheter drainage system.

The present invention also provides a catheter comprising the pH sensor of the present invention. The pH sensor is positioned so that it can be seen by the patient or carer when the catheter is in use. It is preferred that the pH sensor is positioned close to the end of the catheter to be inserted but will still be visible to the patient or carer once the catheter has been inserted. In a particularly preferred embodiment, the pH sensor is positioned at the end of the catheter that in use is connected to the drainage bag tubing. The present invention also provides a drainage unit comprising the pH sensor of the present invention. The pH sensor is positioned so that it can be seen by the patient or carer when the drainage unit is in use. In a particularly preferred embodiment, the pH sensor is positioned at the end of the drainage bag tubing that in use is connected to the catheter.

The present invention also provides a drainage bag comprising the pH sensor of the present invention.

The present invention also provides a connection unit comprising the pH sensor of the present invention, wherein the connection unit can be inserted between the drainage unit and the catheter. The connection unit has the advantage that it can be used with existing catheters and drainage units, is easier and cheaper to manufacture and can easily be replaced without having to replace the catheter or drainage unit.

The present invention also provides the use of the pH sensor of the present invention for predicting impending catheter encrustation and blockage comprising positioning the pH sensor in the flow of urine from a catheter and monitoring for a change in the pH sensor indicating a sustained increase in pH. By predicting impending catheter encrustation and blockage, remedial action can be taken, such as replacing the catheter, to ensure that the catheter does not become blocked. As indicated above, the pH sensor can be positioned within the catheter drainage system at any position provided that it is visible to the patient or carer. In a particularly preferred embodiment, the pH sensor is positioned in the drainage bag. Alternatively, the pH sensor may be positioned within a connection unit that connects the catheter and the drainage unit together.

The present invention also provides a method of the making the pH sensor of the present invention comprising covalently linking the pH indicator to the polymer matrix and then curing the derived composition to form the pH sensor. Preferably, the polymer matrix comprises polyethylene glycol to increase the flexibility of the material and to optimise the response rate of the sensor to an increase in pH.

The specific steps of making the pH sensor will vary depending on the exact pH indicator and polymer matrix used. However, those skilled in the art are aware of suitable techniques for making the pH sensor of the present invention.

The present invention is now described by way of example only with reference to the following figures.

EXAMPLES

Figure 1:
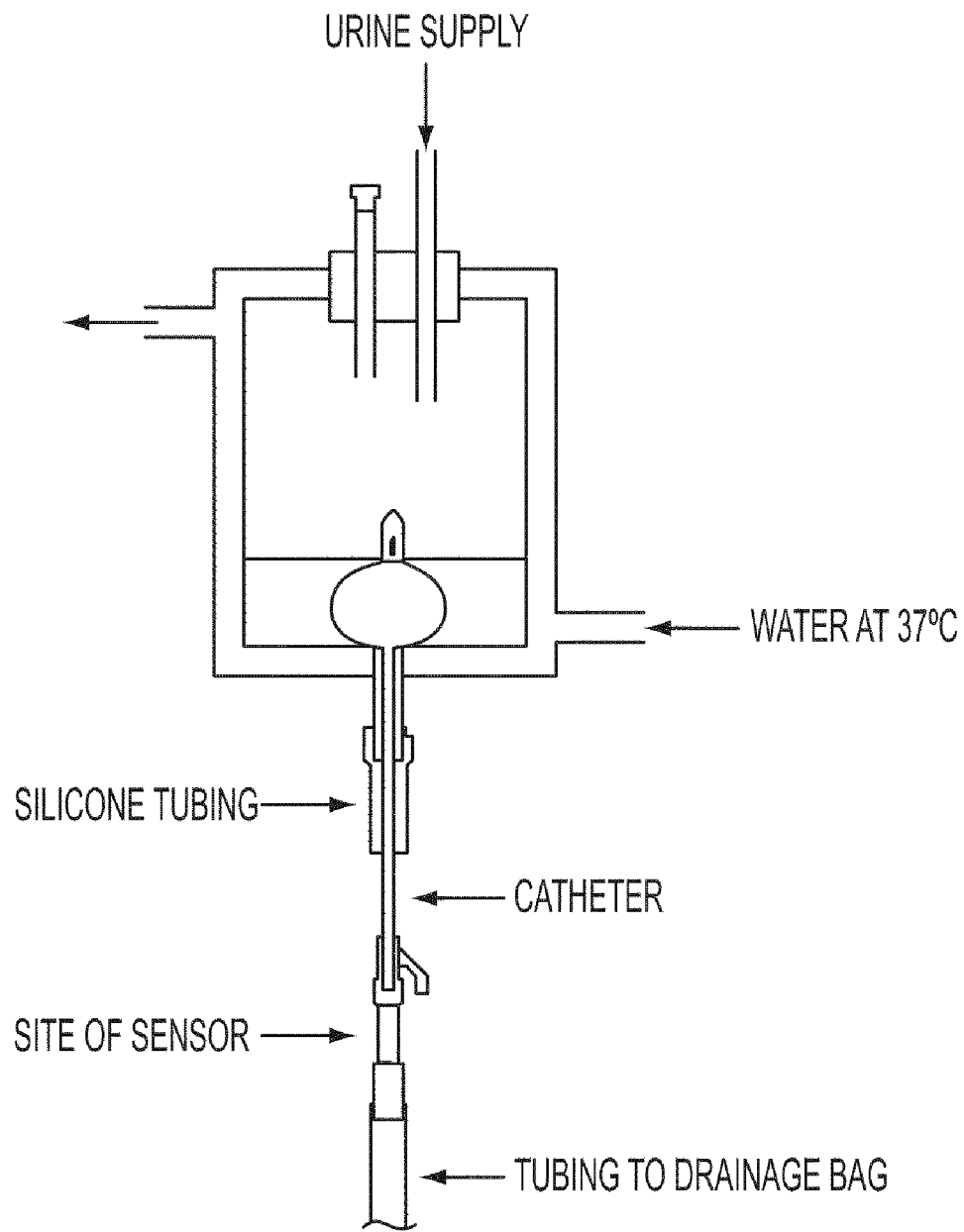
FIG. 1 shows schematically a laboratory model of the catheterised bladder.

To prove the basic concept of the sensor the inventors need to:

1. Demonstrate that the pH indicator in the polymer matrix responds to pH changes at the sensor surface.
2. Demonstrate that the indicator does not leach out of the polymer. That it is stable in the polymer matrix and able to signal the surface pH in a flowing system, for the normal life time of a drainage bag (1 week).
3. Establish that at its preferred site in the drainage bag and the alternative site at the junction of the catheter and the drainage bag tubing, the sensor will signal crystalline biofilm formation on the eye-hole/inflation balloon region, the site at which catheter blockage usually occurs. The drainage bag and the junction of the catheter and the drainage tube have been identified as suitable locations for the sensor because of the requirement for visibility and because it could be fitted into existing drainage systems without necessitating changes to the manufacturing procedures for the catheter.
4. Establish that the sensor signals catheter encrustation well before the catheter blocks.
5. Ensure that any transient changes in the pH of the bulk urine which could result from changes in diet, do not produce false positive signals or confound the response of the sensor to the pH generated by the surface colonising crystalline biofilm.
6. Demonstrate that the sensor does not react when non-urease producing organisms are responsible for urinary infections, but remains capable of signalling any subsequent colonization of the catheterised urinary tract by *P. mirabilis*.

The ability of a pH sensors according to the present invention to meet these specifications has been tested in experiments performed on a laboratory model of the catheterised bladder. The model and its operation has been described in detail previously [4].

Methods and Materials
Chemically Bonding Indicators Via Sulphuric Acid Treatment The method for covalently binding the indicator involved the initial treatment of the indicator in concentrated sulphuric acid. The sulphuric acid converts the hydroethylsulfo groups of the dye into sulfo esters and when the sulphuric acid is eliminated reactive vinylsulfonyl groups are formed. These reactive groups can react with the hydrolysed cellulose (cell-OH) thus chemically binding to the polymeric matrix (see below).

Schematic of the Chemical Structure of Indicator-Cellulose Conjugate

Example 1

Sensor Formulation

Bromothymol blue (BTB)
Cellulose acetate beads (CA)
PEG 5000
Concentrated sulphuric acid
Acetone Cellulose acetate beads are dissolved in acetone (30% cellulose acetate: 70% acetone).

A mixture of BTB and sulphuric acid is prepared (20% BTB w/v) and left for at least 1 hour. The sulphuric acid converts the hydroethylsulfo groups on the BTB into sulfo esters, which can then bind the BTB to hydrolysed cellulose acetate.

A portion of the cellulose acetate that has previously been dissolved in acetone is then mixed with sulphuric acid (10% sulphuric acid) in order to hydrolyse it and is then left for no more than 30 min before use (due to discoloration).

The constituents of the sensor (shown below) are then mixed together vigorously on a glass slab:
Dissolved cellulose acetate (80%)
Sulphuric acid/BTB mixture (1-5%-depending on the concentration of the sensor)
Sulphuric acid/cellulose acetate mixture (10%)
PEG 5000 (5%)

This mixture is then spread evenly over the glass slab and left for 30 min to allow the acetone to evaporate. The sensor is then placed in distilled water overnight to wash away traces of acid.

The sensors are then stored in the fridge prior to use.

The Bladder Model

In essence, the model consists of a glass chamber (1) (200 ml) maintained at 37° C. by a water jacket (3) (FIG. 1). The Model is sterilized by autoclaving and then a catheter (size #14) (5) inserted aseptically into the vessel through sections of silicone tubing (7) attached to a glass outlet at the base. The catheter balloon was inflated with 10 ml of water, securing the catheter in position and sealing the outlet from the "bladder". The catheters was then attached to a drainage tube (11) and reservoir bag. One possible position of the sensor at the catheter-drainage bag tube junction is shown in FIG. 1. Sterile artificial urine was supplied to the bladder via a peristaltic pump. In this way a residual volume of urine (36 ml) collects in the bladder below the level of the catheter eye-hole. As urine continues to be supplied to the model, the overflow drains through the catheter to the collecting bag.

The test organism for these experiments was *P. mirabilis* B2 a clinical isolate from an encrusted catheter. The inoculum for the bladder (1 ml of a young log phase batch culture in the urine medium) was added to 20 ml of residual medium in the bladder and the culture allowed to incubate in the vessel for 1 h to establish itself before the supply of urine at a rate of 0.5 ml/min was switched on. Under these circumstances stable bladder populations of $10^7$-$10^8$ cfu/ml develop in the urine in the bladder chamber.

At the end of the experimental period the supply of urine to the bladder was turned off, the balloon deflated and the catheter removed through the base of the model. The formation of the biofilm and encrustation on the surfaces of the catheters was visualized by scanning electron microscopy.

Results

Figure 2:
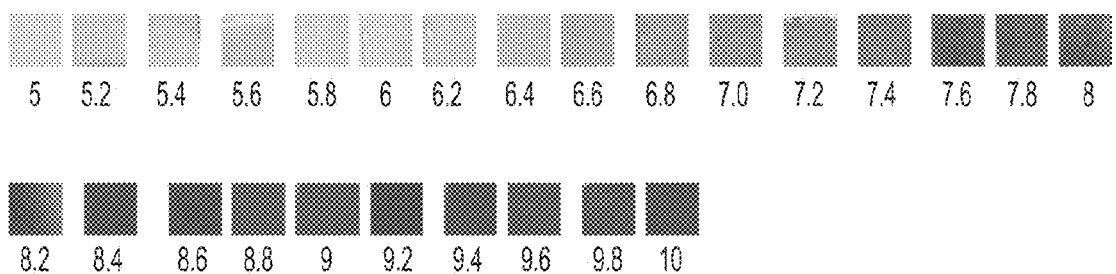
FIG. 2 shows the reaction of the Bromothymol blue/cellulose acetate polymer to 6 h immersion in buffers at pHs ranging from 5.0 to 10.0.

Preliminary experiments with a range of polymer/indicator formulations suggested that the material produced by the covalent bonding of bromothymol blue to cellulose acetate was likely to be suitable for use in the manufacture of the sensor. An image of the response of this material to soaking in a range of pH buffer solutions for 6 h is presented in FIG. 2. The colour transition from yellow to blue (shown here in grayscale) occurs over the range 6.6 to 8.0.

Prototype sensors composed of strips of the bromothymol blue/cellulose acetate polymer were produced, and inserted into drainage bags. They were also formed into rings and inserted into the catheter drainage system at the catheter-drainage bag tube junction.

Performance of the Bromothymol Blue/Cellulose Acetate Sensor in Bladder Models Under Flow Regimes of Buffer Solutions Initially the sensor located at the junction of the catheter and drainage tube was exposed to a flow of buffer (pH 8.0) at 0.5 ml/min for 48 h in the model. A strong visible signal was detected 22 h after exposure to the buffer.

Spectrophotometric methods revealed essentially no elution of the indicator from the polymer over the 48 h.

Figure 3:
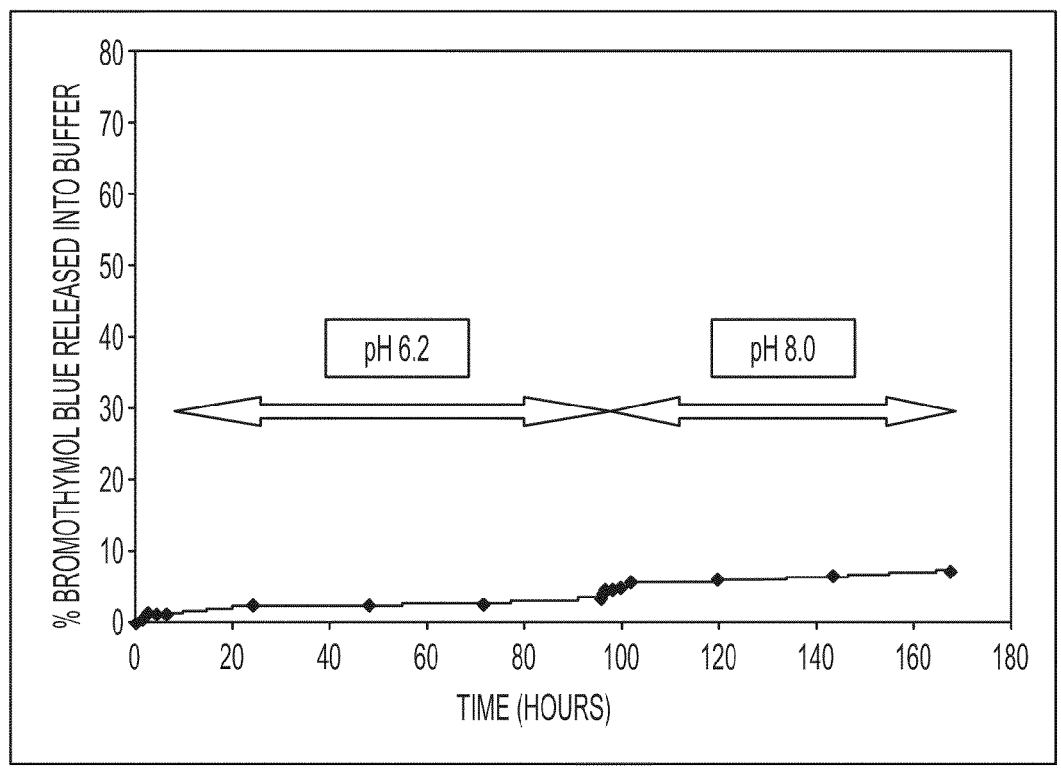
FIG. 3 shows the elution of bromothymol blue from the sensor in flows of buffer at pHs 6.2 and 8.0.

The sensor was also exposed to flows of pH 6.2 buffer for 4 days and then pH 8.0 buffer for a further 4 days. In this case a visible signal was observed 32 h after exposure to the flow of alkaline solution. The data presented in FIG. 3 demonstrate that very little (only 7% of the BTB present in the sensor) eluted from the device on exposure to the flows of buffer for 8 days.

Performance of the Bromothymol Blue/Cellulose Acetate Sensor in Bladder Models Infected with *Proteus mirabilis*

Figure 4:
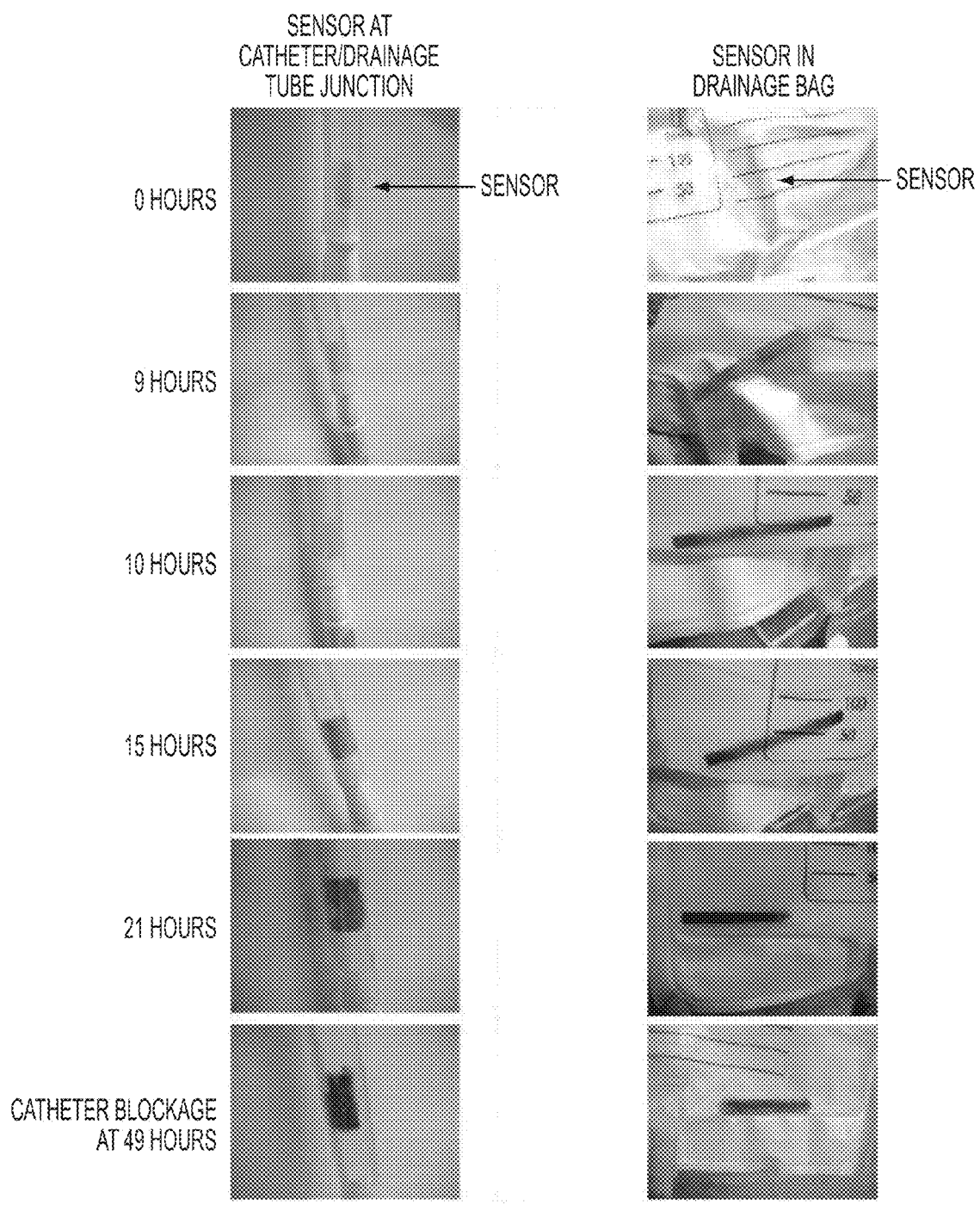
FIG. 4 shows the signal from the pH sensors in bladder models infected with *P. mirabilis*.

Bladder models were fitted with catheter drainage systems containing prototype sensors at the catheter/drainage tube junction and in the drainage bag. The models were supplied with artificial urine and inoculated with *Proteus mirabilis*. The times at which the sensors produced strong visible signals and the times the catheters took to block were recorded. The results of four replicated experiments are summarised in Table 2 and illustrated in FIG. 4. It is clear that the signal from the sensor in the bag was stronger and appeared more rapidly and thus gave earlier warning of catheter blockage. The mean time from the appearance of the signal to the blockage of the catheter being 33 h for the sensor in the catheter/drainage tube junction and 43 h for the sensor in the drainage bag.

TABLE 2

The times sensors took to give signals in bladder models infected with *Proteus mirabilis*

| Experiment Number | Appearance of signal from sensor located at the catheter-drainage tube junction (h) | Appearance of signal from sensor located in the drainage bag (h) | Time at which catheter blockage occurred (h) |
|---|---|---|---|
| 1 | 20 | 12 | 64 |
| 2 | 26 | 16 | 51 |

TABLE 2-continued

The times sensors took to give signals in bladder
models infected with *Proteus mirabilis*

| Experiment Number | Appearance of signal from sensor located at the catheter-drainage tube junction (h) | Appearance of signal from sensor located in the drainage bag (h) | Time at which catheter blockage occurred (h) |
|---|---|---|---|
| 3 | 21 | 10 | 49 |
| 4 | 22 | 11 | 57 |
| Mean | 22.25 | 12.25 | 55.25 |
| Mean time (h) from signal to catheter blockage | 33 | 43 | |

Statistical analysis (t-test) was performed between the data for the means times the signals appeared on the sensor located at the catheter-bag junction and on the sensor in the drainage bag. The t-test produced a significant P value of 0.00076.

Figure 5A:
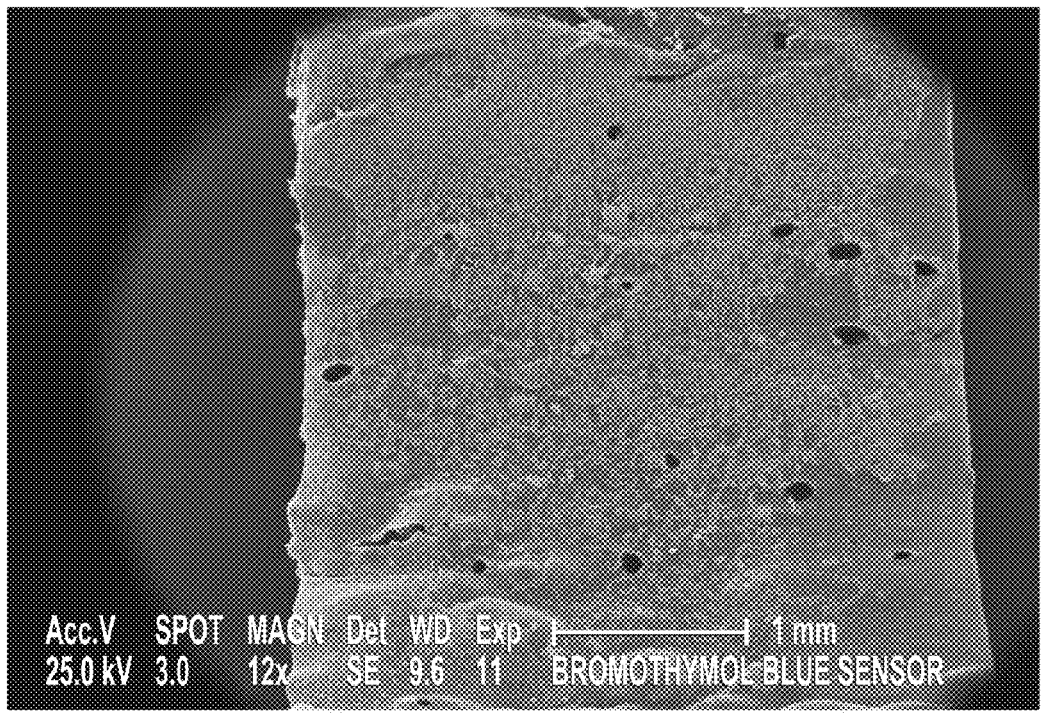
FIG. 5 shows scanning electron micrographs of the sensor after 47 h in the *P. mirabilis* infected model (FIG. 5A is at low magnification (12×) and FIG. 5B is at high magnification (6469×)).
Figure 5B:
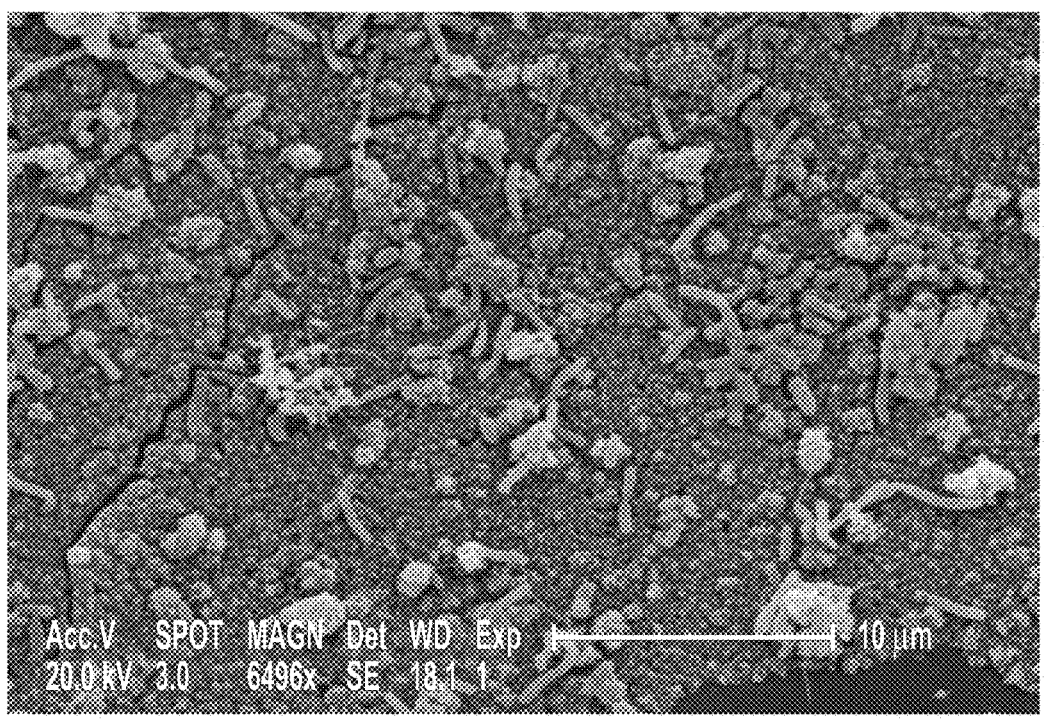

The sensors were removed from the models at the end of the experiment and examined by electron microscopy. The micrographs (FIG. 5) show the presence of bacterial biofilm colonising the sensor. This result is important because it shows that while the biofilm forms most extensively and blocks the catheter at or just below the eye-holes, it also forms on the surface of sensors placed at the catheter/drainage tube junction and in the urine bag, sites that are easily visible to the patient or carer.

Performance of the Bromothymol Blue/Cellulose Acetate Sensor in Bladder Models Infected with *Escherichia coli* and *Proteus mirabilis*

Experiments were performed to test whether the sensors in models infected with organisms that do not generate alkaline urine (eg *E. coli*) are capable of responding to subsequent infection with *P. mirabilis*. Two control models were infected with either *E. coli* or *P. mirabilis*. A third model was infected with *E. coli*, incubated for 48 h and then super-infected with *P. mirabilis*. The control model infected with *P. mirabilis* produced a clear signal at 15 h and the catheter blocked at 59 h. The model infected with *E. coli* alone drained freely for the 120 h of the experimental period and no signal was given by the sensor. In the third model the blue signal became visible at 75 h (27 h after the introduction of the *P. mirabilis*) and the catheter blocked at 117 h.

CONCLUSIONS

1. The BromoThymol Blue/Cellulose Acetate polymer responds clearly to changes in pH over the range 6.6 to 8.0.
2. Sensors prepared from the BromoThymol Blue/Cellulose Acetate polymer take time to respond to the surface pH. They took 20-30 h to respond to the pH of flows of buffer solutions and 12 h to respond to urine infected with *P. mirabilis*. These data indicate that the sensors will not respond to transient changes in the pH of the fluid flowing over them.
3. The BromoThymol Blue does not elute in any quantity from the sensor under flowing conditions. In tests over 8 days only 7% of the indicator in the sensor eluted into buffer solutions.
4. At its preferred location in the drainage bag, the sensor is capable of signalling biofilm formation at the catheter eye-hole. The signal also becomes visible well before (approximately 43 h in infected bladder models) the catheters block.
5. The sensor does not respond when the catheterised urinary tract is infected with organisms which do not produce urease (eg *E. coli*). If *P. mirabilis* subsequently infects such a catheterised tract however, the sensor is able to respond and signal that conditions required for encrustation have been established.

Clinical Trial of the Sensor

Twenty patients undergoing long-term indwelling bladder catheterisation were recruited for the study. Some patients had no encrustation problems others were experiencing frequent catheter blockage. Sterile sensors produced by the method indicated above, were aseptically introduced into newly fitted urine bags. At the time of catheter change, the new catheters were attached to sterile drainage bags fitted with the pH sensors. The bags were changed at the usual weekly intervals. Urine samples were taken at the end of each week for bacteriological analysis and pH measurement. Each patient was followed until their catheter was removed on schedule or because it had blocked. Catheters were examined for encrustation by digital photography and scanning electron microscopy. Photographs were also taken of the sensor after exposure to the urine for 2 and 7 days. The colours registered by the sensor at various pHs in patient's urine were rather darker than in the artificial urine that had been used in the laboratory experiments. The positive signal from the sensor was recognized as a dark blue/black colour. A summary of the results is presented in Table 3.

TABLE 1

Summary of results from clinical study on the sensor

| Patient Group | Number of patients | Number of cases where sensor signalled |
|---|---|---|
| Infected with *P. mirabilis* | 15 | 15 |
| Encrustation found on catheters | 15 | 15 |
| Not infected with *P. mirabilis* | 5 | 0 |
| Catheters showed no signs of encrustation | 5 | 0 |
| Catheters were removed due to blockage | 12 | 12 |
| Catheters were removed on schedule | 8 | 3 |

The sensor signalled all 15 of the cases in which *P. mirabilis* was present in the urine and catheter encrustation was observed. In the 12 cases in which unscheduled removal of the catheter due to blockage was reported, the mean time between the signal (as observed by the visiting nurse) and blockage was 1.8 weeks. There were three cases where the sensor had turned blue/black and yet the catheters drained freely for the scheduled 12 weeks. Examination of each of these catheters, however, revealed the presence of encrustation. In one case the patient acquired a *P. mirabilis* infection in week 5 of the study (during a period of respite care in hospital). Enquiries revealed that subsequent catheters blocked regularly at 3 to 4 week intervals. In the second case the patient became infected with *P. mirabilis* from week 4 onwards. This patient was a young male who made a point of having a high fluid intake. This is an extremely interesting observation in view of laboratory studies showing that a high fluid intake slows the rate of catheter encrustation. In the third of these cases *P. mirabilis* was recovered from the patients urine throughout the 12 weeks and the sensor produced a signal from week 1. Electron micrographs of this catheter show that although it had not blocked, extensive encrustation had taken place.

The results of the pH measurements on the urine revealed many examples when the sensor was dark/blue black in colour yet the urine was acid. Electron microscopy on sensors removed from patients bags showed them to be covered with crystalline biofilm. These observations indicate that the sensor is responding to the pH of the *P. mirabilis* surface biofilm rather than the pH of urine.

CONCLUSIONS

1. The clinical study confirmed that the change in the sensor from golden yellow to dark blue/black indicated that the patient was infected with *P. mirabilis* and that catheter encrustation was occurring.
2. The sensor recorded the pH of the biofilm on its surface rather than the pH of the urine in the bag.
3. In those patients whose catheters blocked the sensor signalled encrustation at a mean time of 1.8 weeks before blockage occurred.

All cited documents are incorporated herein by reference.

REFERENCES

1. Kunin C M, (1989) Blockage of urinary catheters: role of microorganisms and the constituents of urine on the formation of encrustations. Journal of Clinical Epidemiology 42: 835.
2. Morris S N, Stickler D J, McLean R J C, (1999) The development of bacterial biofilms on indwelling urethral catheters. World Journal of Urology, 17: 345.
3. Kohler-Ockmore J, Feneley R J C (1996) Long-term catheterisation of the bladder: prevalence and morbidity. British Journal of Urology, 77: 347-351.
4. Stickler D J, Morris N S, Winters C, (1999) Simple physical model to study formation and physiology of biofilms on urethral catheters. Methods in Enzymology 310: 494.

The invention claimed is:

1. A pH sensor configured for incorporation into a catheter drainage system wherein the pH sensor comprises:
   a polymer matrix chemically bound to a pH indicator, wherein the pH indicator only responds to sustained contact with a liquid or biofilm at an increased pH.

2. The pH sensor according to claim 1, that is configured to be incorporated into a catheter drainage system at any position provided that during use said pH sensor is visible.

3. The pH sensor according to claim 1 or claim 2 that is formed as a disc for insertion into a drainage bag of a catheter drainage system.

4. The pH sensor according to claim 1 or claim 2, that is formed as an annular ring having a bore allowing fluid to pass through the pH sensor.

5. The pH sensor according to any one of claims 1 and 2, wherein the polymer matrix is polyurethane or cellulose acetate.

6. The pH sensor according to any one of claims 1 and 2, wherein the pH indicator changes colour in response to an increase in pH of a bacterial biofilm that develops on the pH sensor.

7. The pH sensor according to any one of claims 1 and 2, wherein the pH indicator changes colour in response to an increase in pH from pH 6 to pH 7.6 or above.

8. The pH sensor according to any one of claims 1 and 2, wherein the pH indicator is selected from the group consisting of bromocresol purple, chlorophenol red, neutral red, bromothymol blue, cresol red, m-cresol purple, phenol red, 3-(m-)nitrophenol, thymol blue, cresolphthalein, fluorescein, Rosolic acid, and α-naphtholbenzene.

9. The pH sensor according to any one of claims 1 and 2, wherein the pH indicator is selected from the group consisting of neutral red, bromothymol blue, cresol red, phenol red, 3-(m-)fluorescein and rosolic acid.

10. The pH sensor according to any one of claims 1 and 2, wherein the sustained contact is more than 6 hours.

11. The pH sensor according to any one of claims 1 and 2, wherein the sustained contact is more than 9 hours.

12. The pH sensor according to any one of claims 1 and 2, wherein the sustained contact is more than 12 hours.

13. The pH sensor according to claim 1, which additionally comprises a matrix stabiliser.

14. The pH sensor according to claim 13, wherein the matrix stabiliser is a quaternary ammonium compound.

15. The pH sensor according to claim 1, wherein the polymer matrix is cellulose acetate and the pH indicator is bromothymol blue.

16. The pH sensor according to any one of claims 1 and 2, which is provided with a reference material to assist in determining when the pH indicator has responded to a sustained increase in pH.

17. A catheter comprising a pH sensor according to any one of claims 1 and 2 wherein the pH sensor is incorporated at any position in the catheter provided that during use said catheter is visible to a patient or caregiver.

18. A drainage bag comprising a pH sensor according to any one of claim 1, 2, 13, 14, or 15.

19. The catheter according to claim 17, wherein the pH sensor is positioned at an end of the catheter, wherein when in use the end is connected to a drainage unit.

20. A drainage unit comprising a pH sensor according to any one of claim 1, 2, 13, 14, or 15.

21. The drainage unit according to claim 20, wherein the drainage unit comprises a drainage bag and drainage bag tubing, and the pH sensor is positioned at an end of the drainage bag tubing, wherein when in use the end is connected to the catheter.

22. A connection unit comprising the pH sensor according to any one of claim 1, 2, 13, 14, or 15, wherein the connection unit can be inserted between a drainage unit and a catheter.

23. A method of predicting impending catheter encrustation and blockage comprising:
   positioning the pH sensor of claim 1, 2, 13, 14, or 15 in a flow of urine from a catheter and visually monitoring the pH sensor for a change indicating sustained contact with urine or a biofilm at increased pH.

24. A method of making a pH sensor according to any one of claim 1, 2, 13, 14, or 15, comprising:
   linking the pH indicator to the polymer matrix to form a composition and then curing the composition to form the pH sensor.

25. The method of claim 24, wherein the polymer matrix comprises polyethylene glycol.

26. The method of claim 23, wherein the sustained contact is more than 6 hours.

27. The method of claim 23, wherein the sustained contact is more than 9 hours.

28. The method of claim 23, when the sustained contact is more than 12 hours.

29. The method of claim 24 wherein the linking is a covalent linking.

30. The pH sensor of claim 1 wherein the polymer matrix is covalently bound to the pH indicator.

* * * * *